United States Patent [19]

Vaicaitis

[11] Patent Number: 4,644,794
[45] Date of Patent: Feb. 24, 1987

[54] ACOUSTIC GUIDE FOR NOISE-TRANSMISSION TESTING OF AIRCRAFT

[75] Inventor: Rimas Vaicaitis, New York, N.Y.

[73] Assignee: The United States of America as represented by the Administrator of the National Aeronautics and Space Administration, Washington, D.C.

[21] Appl. No.: 751,695

[22] Filed: Jul. 3, 1985

[51] Int. Cl.$^4$ ............................................. G01N 29/00
[52] U.S. Cl. ....................................... 73/583; 73/589; 73/599
[58] Field of Search .................. 73/583, 589, 591, 599

[56] References Cited

U.S. PATENT DOCUMENTS

| | | | |
|---|---|---|---|
| 3,254,739 | 6/1966 | Hardy | 73/599 |
| 3,470,734 | 10/1969 | Agdur et al. | 73/32 A |
| 4,204,432 | 5/1980 | Pujolle et al. | 73/599 |
| 4,289,032 | 9/1981 | Tominaga et al. | 73/599 |
| 4,366,712 | 1/1983 | Bathmann et al. | 73/599 |
| 4,397,187 | 8/1983 | Stribling | 73/589 |

Primary Examiner—Anthony V. Ciarlante
Attorney, Agent, or Firm—George F. Helfrich; Howard J. Osborn; John R. Manning

[57] ABSTRACT

The invention is an apparatus which allows selective testing of aircraft or other vehicular components without requiring disassembly of the vehicle or components. The invention consists of a broad-band noise source 11, a guide 12 to direct the acoustic energy, soft sealing insulation 17 to seal the guide to the noise source and to the vehicle component, and noise measurement microphones 13, 14, both outside the vehicle at the acoustic guide output and inside the vehicle to receive attenuated sound. By directing acoustic energy only to selected components of a vehicle via the acoustic guide, it is possible to test a specific component, such as a door or window, without picking up extraneous noise which may be transmitted to the vehicle interior through other components or structure. This effect is achieved because no acoustic energy strikes the vehicle exterior except at the selected component. Also, since the test component remains attached to the vehicle, component dynamics with vehicle frame are not altered.

15 Claims, 4 Drawing Figures

ACOUSTIC GUIDE FOR NOISE-TRANSMISSION TESTING OF AIRCRAFT

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

TECHNICAL FIELD OF THE INVENTION

The invention is related to the acoustic and noise testing technology field.

BACKGROUND OF THE INVENTION

There is a long felt and continuing need in the aircraft industry to control and reduce interior noise levels in aircraft and other vehicles. This need is constrained by restrictions in weight, in volume and in cost. Nevertheless, lack of effective noise control results in operator and passenger fatigue and discomfort. Often, noise also creates a hazard, either by distraction or by direct interference, for example interference with intra-cockpit or radio communications. Additionally, high noise levels excite vibrational modes in aircraft structures and skin materials resulting in mechanical wear and stress. Because of the wear and stress, heavier structures are required with the accompanying penalties of larger engines, more fuel, etc.

Solutions to aircraft noise problems have been difficult partially because of the complex interaction of noise frequencies traveling through the interior cabin air and through the structures of aircraft. Control of noise being transmitted through the interior cabin airspace is basically a function of (1) isolation breaking the acoustic path, (2) insulation with mass for low frequency noise and (3) damping with multi layers of soft material for higher frequency noise. Control of noise being transmitted by the vehicle structure is basically a function of (1) providing discontinuities in the hard structures and (2) introducing resilient joints between structural components. Control of both types of transmission is also affected by the acoustic impedance of boundary materials, that is, the ratio of sound pressure to the corresponding particle velocity at the boundary surface. The above factors interact to determine whether noise will be transmitted from the outside air to the aircraft skin and structural components, where noise will be conducted within the structures, and whether it will be re-emitted into the interior air of the aircraft.

Compounding the intractability of the noise problem has been a lack of adequate acoustic test devices. Prior art methods have included two basic methods of testing. In the first method specific aircraft parts or materials are tested in various small acoustic chambers. A piece of carpeting, panel or door, for example can be tested in order to compare one sample against another. Unfortunately, this method frequently interferes with the normal vibrational dynamics of the installed sample. Further, this method fails to account for sound path conduction and re-emission. For example, an aircraft door may pick up external noise and transmit it structurally through hinges and latching mechanisms to other parts of the aircraft where the noise is re-emitted into the cabin space. This phenomenon may occur despite heavy acoustic insulation within the door which prevents direct noise transmission into the cabin.

In the second general method of testing, an assembled aircraft is instrumented and tested as a unit. This testing can be accomplished either by flight or wind tunnel testing or by using large static acoustic chambers. By this method the difficulties of changing vibrational dynamics and of severing noise conduction channels are avoided. However, the inability to restrict noise impingement to selected portions of the aircraft prevents accurate determination of the noise source. Gross noise levels can be determined, but the source cannot. For example, in a large test chamber, noise impinging the entire aircraft may be picked up by a tail surface, transmitted by longeron to the cabin area, and emitted into the cabin air space despite the presence of multiple layers of acoustic insulation within the cabin walls.

Accordingly, it is an object of the present invention to provide a method which will allow testing of an assembled vehicle while retaining the ability to selectively exclude parts of the vehicle from direct sound impingement.

Another object of the present invention is to provide a device to accomplish selective, full-scale acoustic testing.

It is a further object of the present invention to provide a method to accomplish selective testing of a aircraft or vehicular component, such as a door or window, without removing the component from the vehicle and without disrupting conductive sound paths.

Yet another object of the present invention is to provide a device, containing a noise source, an acoustic guide to selectively direct noise impingement, and measurement microplanes, which will allow acoustic testing and analysis of vehicular components.

STATEMENT OF THE INVENTION

According to the present invention, the foregoing and other objects are attained by providing a noise source capable of reproducing operational noise levels, an acoustic wave-guide and seals at the aircraft end and noise-source end of the guide.

In the preferred embodiment of the present invention, the noise source is an audio speaker having an attached rectangular wave guide. The wave guide is insulated from the speaker by soft insulating material. The wave guide is further insulated externally by a sound barrier to prevent external leakage. A soft material is also used to seal the wave guide to the aircraft fuselage to avoid external leakage. Instrumentation of the experimental set-up requires one pick-up microphone inside the wave guide near the aircraft as an input baseline, and one microphone inside the aircraft cabin as a data pick-up for the degree of attenuation. An adjustable support apparatus is also included to allow placement of the test device at various locations on the aircraft structure.

BRIEF DESCRIPTION OF THE DRAWINGS

For a more complete understanding of the present invention and of the inherent advantages thereof, reference is now made to the following description taken in conjunction with the accompanying drawings wherein.

DETAILED DESCRIPTION OF THE INVENTION

Figure 1:
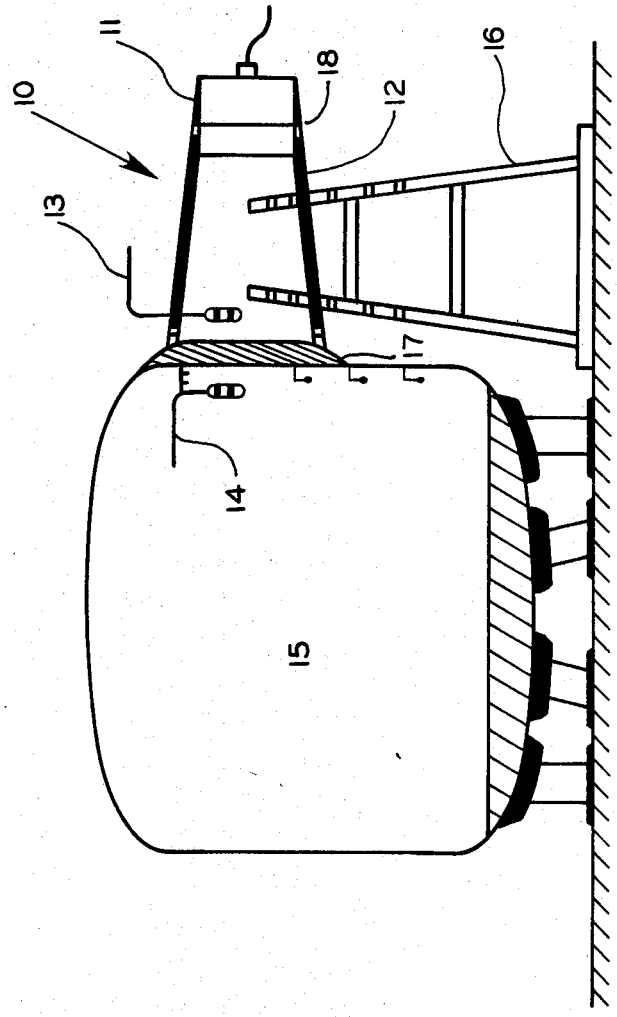
FIG. 1 is a sectional side view of the present invention attached to an aircraft fuselage and set-up for experimental use.

Referring now to the drawings wherein the same element is referred to by the same numeral throughout the several views and more particularly to FIG. 1, the preferred embodiment of the present invention is depicted and designated generally by the numeral 10. The acoustic test device 10 is comprised of an audio speaker 11 attached to an acoustic guide 12. An output microphone 13 is installed at the test end of the guide and an attenuation measurement microphone 14 is located inside the aircraft cabin 15. An adjustable support 16 allows placement of the test device 10 in various locations outside cabin 15. Acoustic seals are installed at the aircraft-guide interface 17 and at the speaker-guide interface 18. In a typical test sequence, noise signals for specific phases of flight are generated and transmitted via the acoustic guide 12 to the impingement point on the aircraft. Just prior to impingement, the output monitor microphone 13 records the actual frequencies and power levels. Direct passage of acoustic energy is recorded by the monitor microphone 14 inside the cabin wall. Because the test noise is contained within the acoustic guide 12, noise striking other areas on the aircraft is minimized so as to prevent lateral conduction of external noise along aircraft structural elements. This isolation effect allows selective testing of the specific aircraft section. At the same time, conduction effects emanating from the specific section being tested can be evaluated. For example, installed testing capability allows detection of noise impinging on the exterior of the passenger cabin wall and then being conducted via longerons or other structure to other locations in the vehicle.

Figure 2:
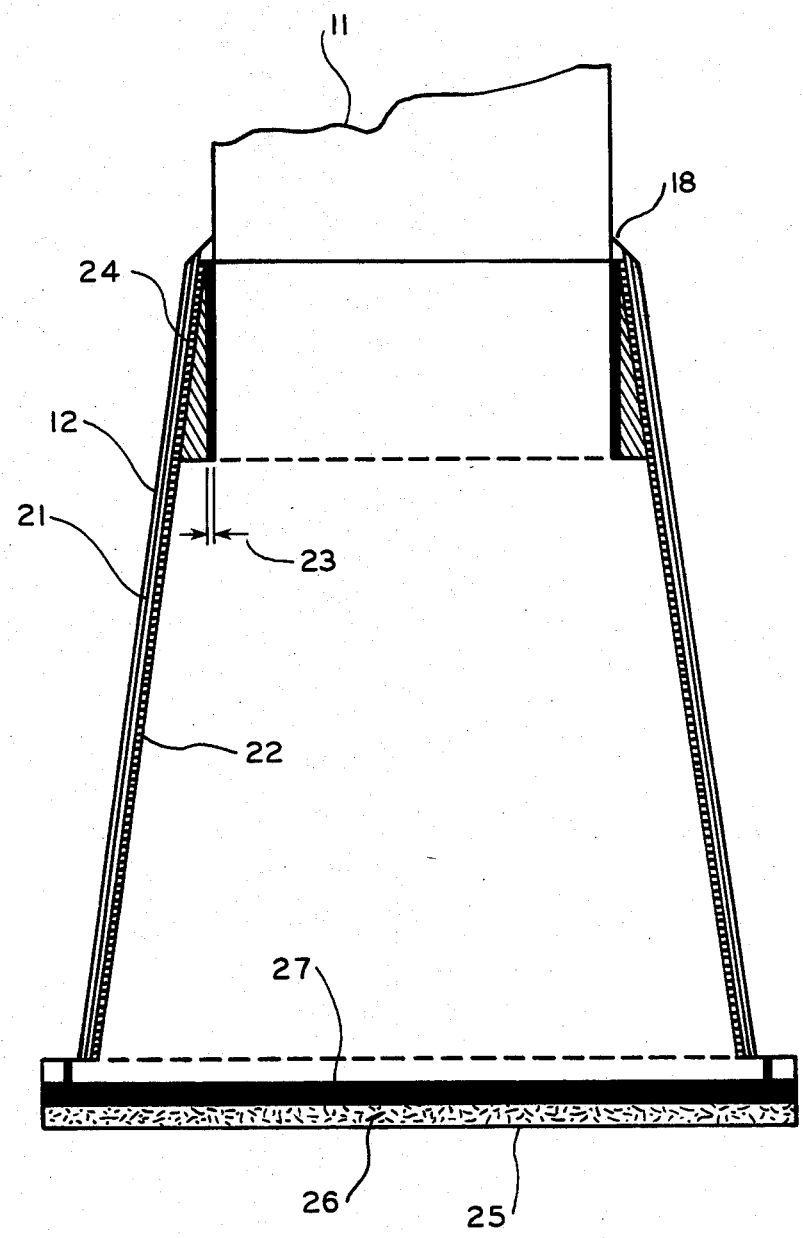
FIG. 2 is a sectional side view of the acoustic guide assembly with general construction details.

The details of the acoustic guide construction can be more readily seen by reference to FIG. 2 depicting a cross-sectional side view of the guide 12. In partial cross-section, speaker 11 is attached to the guide at the guide input end 18. Acoustical insulation 21 constructed with polystyrene sheeting is installed along the guide 12, while the inner layer of guide 12 is constructed of plywood 22 to provide structural rigidity and to provide a reflective surface inside the acoustic guide. Further insulation is installed around speaker 11 in the form of $\frac{1}{8}$-inch foam rubber 23 and shim wedges 24. Similarly, on the output end 25 of the acoustic guide, acoustic foam 26 forms the seal between the aircraft and the gasket 27 on the guide. It should be understood that the seal can be shaped to conform to the various contours of the object being tested.

For the purpose of illustration, dimensions of the preferred embodiment, sized to allow testing of aircraft windows and like-sized components is 24 inches in height and width across the face of speaker 11. The length of the acoustic duct as designed is 26 inches. These dimensions can be changed to test components of different sizes. In the preferred embodiment, an expanding extension section was added to the acoustic guide for the purpose of testing larger components.

Figure 3:
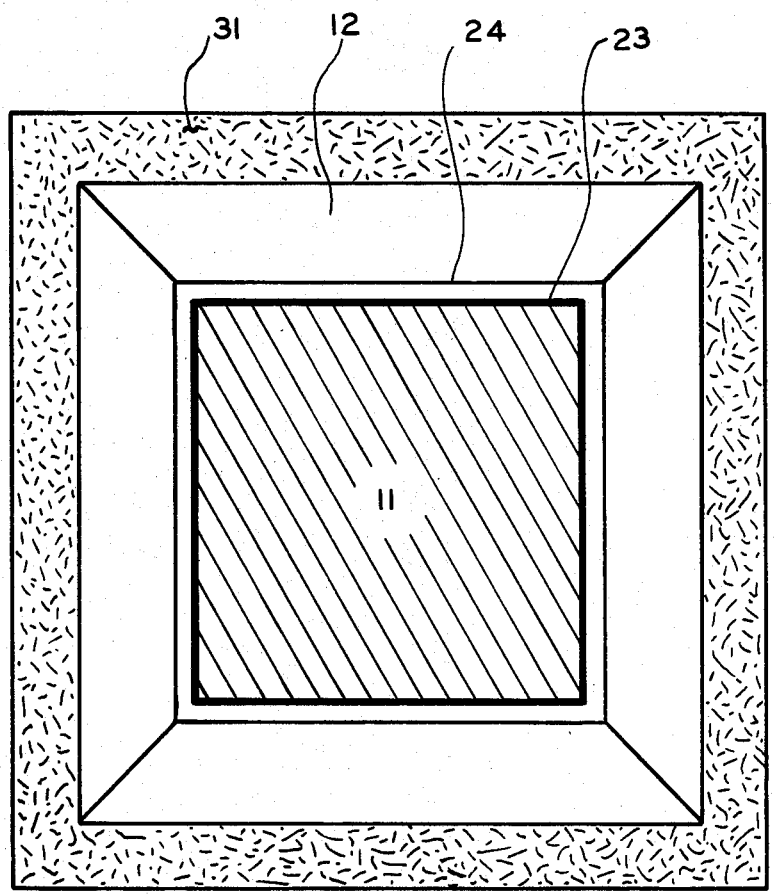
FIG. 3 is an end view of the acoustic guide with specific construction details.

FIG. 3 shows an end view of the output end of the acoustic guide 12 with the dimensions of the preferred embodiment.

OPERATION OF THE INVENTION

The present invention allows acoustic testing of vehicle components, such as doors, windows, and cabin walls without requiring disassembly of the vehicle or components. FIG. 1 depicts a representative test configuration. The invention 10 consists of a speaker 11, a lightweight acoustic guide 12 and monitoring equipment, 13 and 14. The acoustic guide is used to direct the test signal on to specific parts of the vehicle and at the same time prevent sound impingement on other parts of the vehicle. The entire design is low cost, lightweight, and portable.

During a typical test, the present invention is set up to direct noise energy on to a component of the vehicle, such as a window. Using a dual-input strip chart recorder, a record is made of the frequency and amplitude of the noise directed against the component and of the frequency and amplitude of the noise passing through the component. The strip-chart then provides a direct readout of attenuation of noise and permits an easy comparison of the effects of modification in insulating material.

By analyzing the noise attenutation over the frequency range, a determination of the source of the noise and the best method of insulation can be made. For example, high frequency noise can be attenuated by use of soft inner liners and porous material. Low frequency noise, in contrast, is little affected by soft insulation. Low frequency noise tends to be picked up by structural members and transmitted. This structurally transmitted noise can be attenuated by use of mass for insulation or by the isolation of noise paths. One frame member can be isolated from another by rubber spacers, for example.

Similarly, by analyzing the spectral characteristics of the interior noise, a determination of the source of the sound can be made. Generally, lower frequencies tend to be structurally transmitted whereas higher frequencies tend to be transmitted through the air within the vehicle.

In the completion of an acoustic analysis, the present invention 10 is re-located to a number of points outside the test vehicle. Where testing near the cabin generally determines the noise pass-through of the cabin wall, testing near the tail surfaces of an aircraft will help determine structurally transmitted noise sources. In this way, the effects in the cabin caused by turbulent airstream noise on the tail can be simulated.

Figure 4:
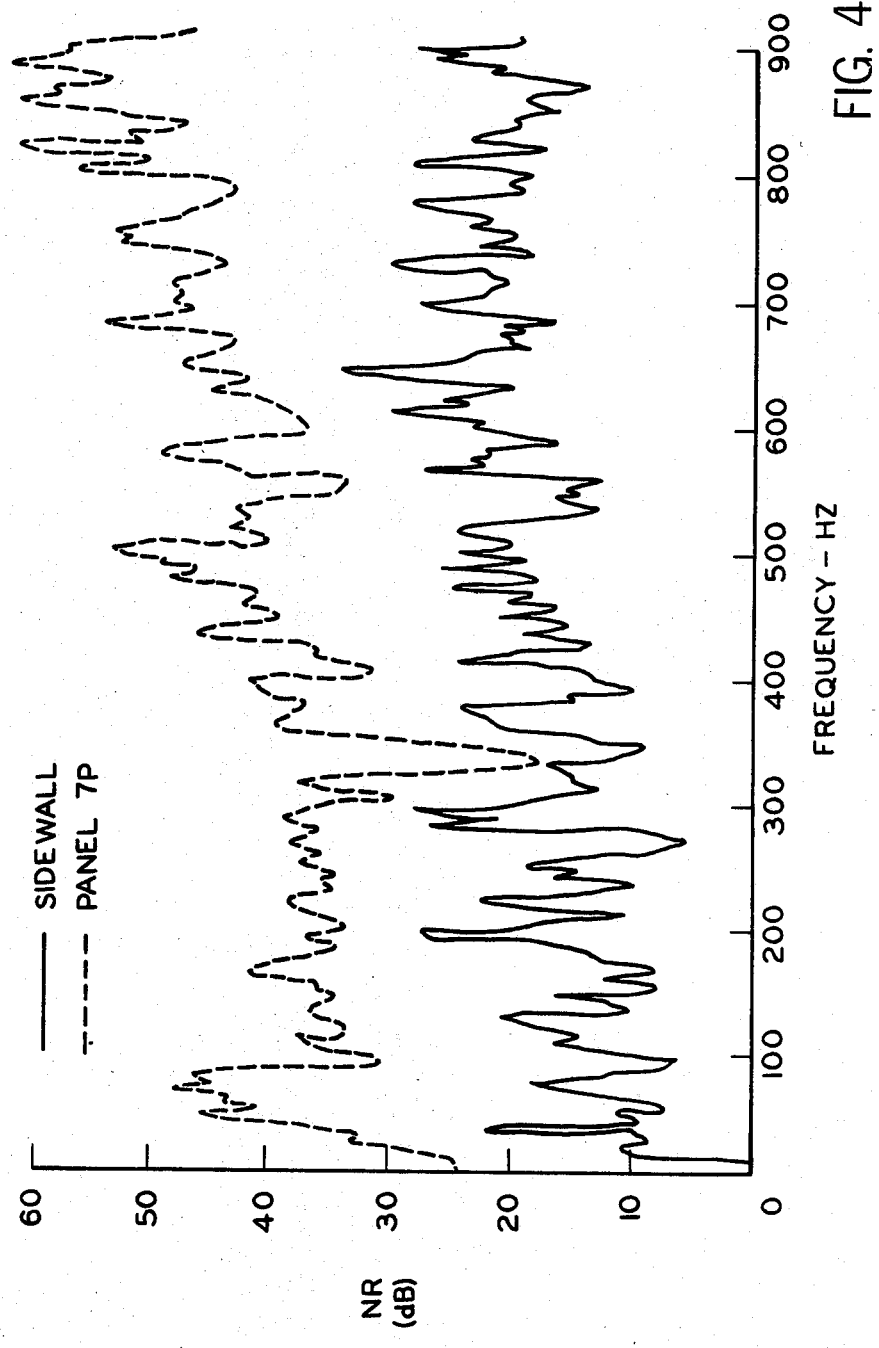
FIG. 4 is a sample of data produced by the present invention showing the attentuation of noise resulting from the addition of insulating material.

By using the present invention to acoustically test each section of the vehicle, a frequency-matched attenuation chart can be developed for the vehicle from which a determination can be made of the location of noise and the type of attenuation techniques which are needed. FIG. 4 is a representative sample of such a chart. On FIG. 4 the solid line on the lower position of the chart shows the noise attenuation through the vehicle wall, while the upper dotted line shows the noise attenuation through the wall with an insulating panel attached to the wall.

I claim:

1. A method for acoustic testing of interior cabin noise levels in assembled, full-scale vehicles which allows selective testing of installed components and subassemblies comprising the following steps:

sealing an acoustic guide to a noise source and to a test component such that noise impingement is restricted to the test component only;

transmitting noise into the acoustic guide;
directing said noise from the acoustic guide on to a component or subassembly of a test object;
measuring noise energy delivered to the exterior of the test component;
measuring noise energy transmitted through the test component into the interior of the test object;
modifying the noise transmission characteristics of the test component;
measuring new noise levels transmitted to the test object interior through the modified test component;
comparing interior noise level results to determine noise transmitted.

2. A method as in claim 1 wherein the step of sealing the acoustic guide consists of forming appropriately shaped shims or gaskets from wood materials and further isolating these seals with a thin layer of foam rubber.

3. A method as in claim 1 wherein the steps of measuring test output noise levels and noise levels inside the cabins are accomplished by recording these values as picked up by omni-directional microphones.

4. A method as in claim 1 wherein the step of modifying the noise transmission characteristics consists of adding insulation.

5. A method as in claim 1 wherein the step of modifying the noise transmission characteristics consists of adding porous material to the test object interior.

6. A method as in claim 1 wherein the step of modifying the noise transmission characteristics consists of isolating frame members and other structural materials from direct contact with one another by installation of resilient spacers.

7. A method as in claim 1 wherein the step of modifying the noise transmission characteristics consists of damping of noise frequencies by altering the resiliency of interior wall surfaces.

8. A method as in claim 1 wherein the test object is an aircraft.

9. An apparatus for acoustic testing of interior noise levels in a full-scale assembly of a vehicle which allows selective testing of components and subassemblies comprising the following:
a noise source;
an acoustically-insulated guide;
acoustic seals between the noise source and the acoustic guide and between the guide and a test component;
noise monitors within the guide and within the vehicle assembly interior;
means for comparing noise levels within the guide with those within the vehicle assembly;
means for adjusting the location of the acoustic testing apparatus with respect to the full-scale assembly.

10. An apparatus for acoustic testing as in claim 9 wherein the full-scale assembly is an aircraft.

11. An apparatus for acoustic testing as in claim 9 wherein the noise source is a broad-band audio speaker.

12. An apparatus for acoustic testing as in claim 9 wherein the assembly interior is a vehicle cabin.

13. An appratus for acoustic testing as in claim 9 wherein the means for adjusting the location of the acoustic testing apparatus is an adjustable support stand.

14. An apparatus for acoustic testing as in claim 9 wherein the acoustically-insulated guide consists of a wooden enclosure insulated with polystyrene.

15. An apparatus for acoustic testing as in claim 9 wherein the noise monitors consist of omni-directional microphones.

* * * * *